| United States Patent [19] | [11] Patent Number: 4,546,201 |
| Piccolo et al. | [45] Date of Patent: Oct. 8, 1985 |

[54] PROCESS FOR THE OPTICAL RESOLUTION OF (±)2-(6'METHOXY-2'-NAPHTHYL)-PROPIONIC ACID

[75] Inventors: Oreste Piccolo, Leghorn; Giovanni Villa, Monticello; Enrico Zen, Macherio, all of Italy

[73] Assignee: Blaschim S.p.A., Milan, Italy

[21] Appl. No.: 602,744

[22] Filed: Apr. 23, 1984

[30] Foreign Application Priority Data

Jul. 27, 1983 [IT] Italy ................ 22261 A/83

[51] Int. Cl.⁴ .............................. C07B 19/00
[52] U.S. Cl. .................... 562/401; 562/466
[58] Field of Search ................ 562/401, 466

[56] References Cited

U.S. PATENT DOCUMENTS

| 3,686,183 | 8/1972 | Dyson | 562/401 X |
| 3,766,264 | 10/1973 | Schaaf et al. | 562/401 |
| 4,209,639 | 6/1980 | Nicholson et al. | 562/401 |
| 4,224,457 | 9/1980 | Iwao et al. | 562/401 |

FOREIGN PATENT DOCUMENTS 0072040  2/1983  European Pat. Off. .
55-135   4/1980  Japan .

*Primary Examiner*—Natalie Trousof
*Assistant Examiner*—Vera C. Clarke
*Attorney, Agent, or Firm*—Cushman, Darby & Cushman

[57] ABSTRACT

Process for the optical resolution of (±)2-(6'methoxy-2'-naphthyl)-propionic acid by adding from 0.45 to 0.65 mole of (S)-alpha-phenylethylamine to each mole of said acid in chloroform.

4 Claims, No Drawings

PROCESS FOR THE OPTICAL RESOLUTION OF (±)2-(6'METHOXY-2'-NAPHTHYL)-PROPIONIC ACID

This invention relates to a process for the optical resolution of (±) 2-(6'-methoxy-2'-naphthyl)-propionic acid, hereinafter indicated conventionally as (±) AMNP, by means of (S)-alpha-phenylethylamine, hereinafter indicated conventionally as PEA.

More particularly this invention relates to a process which comprises (a) the addition of from 0.45 to 0.65 mole of (S)-alpha-phenylethylamine to each mole of the acid in 3 parts ±15%, with regard to the acid, of chloroform at from 0° to 58° C., (b) the subsequent cooling of the reaction mixture to 0° C., (c) the filtration of the thus obtained precipitate, (d) the suspension of the filtrate into chloroform at 15°–58° C., (e) the subsequent cooling of the reaction mixture, (f) the filtration of the thus obtained precipitate, (g) the further suspension of the precipitate into chloroform and its treatment with an aqueous alkaline solution, (h) the separation of the chloroform phase from the aqueous phase, (i) the treatment of the latter with acid to afford (+) 2-(6'-methoxy-2'-naphthyl)-propionic acid and its recovery by usual techniques.

(+) AMNP, whose non-proprietary name is Naproxen, is a known drug endowed with anti-inflammatory, anti-pyretic and analgesic activity.

BACKGROUND OF THE INVENTION

The separation of the enantiomers of an acid or a base or the formation of a salt with an optically active base or acid respectively is an elementary knowledge in the art.

On the contrary, there are no further generally applicable pieces of information which allow the chemist to anticipate what are the critical conditions which allow one to separate the enantiomers of a given acid or of a given base on an industrial scale in the most economical way. The finding of these conditions is a largely empirical science which involves overcoming technical prejudices and the original solution of specific technical problems.

The parameters which must be taken into consideration for evaluating if a process of optical resolution is economical on industrial scale are the following:

1. optical purity of the obtained product;
2. yield of the optically active product;
3. productivity (employed volume/amount of treated product ratio);
4. cost of the resolving agent which is used;
5. recoverability of the resolving agent which is used;
6. cost of the recovery of the resolving agent which is used;
7. cost of the solvent or of the solvents mixture which is used;
8. recoverability of the solvent(s) which is (are) used;
9. cost of the recovery of the solvent(s) which is (are) used.

Because of the large therapeutic importance of Naproxen, many methods have been suggested until now for separating the optical isomers of (±) AMNP with optically active bases.

Phenylethylamine or PEA is indicated in some known publications as one of the optically active bases which may be used for separating (±) AMNP.

Among these publications, those which do not indicate the experimental conditions represent information devoid of any value to the artisan.

On the contrary, those which indicate specific operative conditions do not offer such an advantage as to encourage further investigations.

In U.K. Patent Specification No. 1,296,493, PEA is mentioned in generic terms as one of the many optical active bases which may be used for separating (±) AMNP but there is no suggestion concerning the proper solvent, the specific operative conditions, the optical purity of the thus obtained product, the productivity of the process or the recoverability of the solvent and/or of PEA.

U.S. Pat. No. 4,209,638 discloses a process for increasing the amount of a desired enantiomer in a racemic mixture of an arylpropionic acid. (±) AMNP and PEA are mentioned among the possible acids and bases, respectively. The solvent used is a petroleum fraction which begins to boil at 112° C. In accordance with the aim of the patent, an AMNP is obtained which is only slightly enriched with respect to (±) enantiomer and the specification does not mention what kind of and how many further treatments are necessary to obtain a product having the desired optical purity.

European Patent Application No. 82200512.0 discloses a process wherein the resolution with PEA is carried out in water. This process has an unfavourable low productivity (solvent/substrate ratio about 17) and requires repeated crystallizations before obtaining a product having the required optical purity.

Japanese non-examined application No. 50/55,135 conjectures the use of many solvents, inclusive of chloroform, and of a quantity of PEA from 0.5 to 1 mole with respect to one mole of (±) AMNP but it indicates as preferred conditions the use of a mixture of methyl alcohol and ethyl acetate, as solvent, and of one mole of PEA for each mole of (±) AMNP. With this conditions the productivity is about 13 and the yield of (+) AMNP having an optical rotatory power of +66.0 (c=1%, chloroform) is only 48% whereas the yield of AMNP having an optical rotatory power of +63.4 is only 56%.

Furthermore, the artisan appreciates immediately the disadvantages connected with the recovery of the solvents. PEA and (−) AMNP. In fact, (−) AMNP and PEA can not be recovered from the mother liquors by simple addition of acids or bases until they contain methanol; on the other hand the removal of the latter, by distillation, from the mother liquors involves also the removal of ethyl acetate because their boiling points are very close and they form an azeotropic mixture. It is therefore self-evident that the low productivity, low yield and high recovery costs do not make this process economical on an industrial scale. Furthermore, the fact that in this patent application is pointing out these conditions as the best ones discourages the technician from investigating all the other innumerable conditions which are mentioned in generic terms in the Japanese Patent Application No. 50/55,135.

Finally, it is known in the art that the maximum resolving power is usually reached when 1 mole of optical active base is used for each mole of racemic acid or, when using a less optically active base, by completing the salt formation by adding another base.

DETAILED DESCRIPTION OF THE INVENTION

It has been now surprisingly found that the behaviour of PEA in chloroform and in the presence of (±) AMNP shows an anomaly that has not yet been reported. It is consisting in the fact that, by keeping the volume of the solvent constant, the resolution capacity increases as the amount of PEA decreases from 1 mole to 0.45-0.65 mole for each mole of (±) AMNP without requiring any adjustment of the missing quantity by addition of another base.

This finding allowed us to develop the process of the instant invention which offers the following advantages:

high yield (70-80%) of (+) AMNP having a rotatory power between +63.0 and +66.0 (c=1%; chloroform);

high productivity (solvent/(±) AMNP ratio = 3 l/kg±15%);

use of one base that at the end of the process is easily recovered (Yield≧90%) in chloroform solution ready to recycle;

use of a single organic solvent which may be easily recovered and recycled;

easy recovery of the remaining mixture of AMNP enriched in (−) AMNP from the mother liquors by treatment with alkalies; after removal of the organic phase, an aqueous alkaline solution is obtained which affords, simply by heating, (±) AMNP which is recycled.

Hereinafter are given some Examples which intend to illustrate this invention without limiting it. In addition are given other Examples concerning different experimental conditions in order to show the advantages of the process according to this invention.

DESCRIPTION OF THE PREFERRED EMBODIMENTS

More particularly Examples 1 and 2 show some typical procedures according to this invention.

Examples from 3 to 5 show the effect of the variation of the PEA/(±)AMNP ratio on the resolution capability when the solvent/(±)AMNP ratio is maintained constant. Using a ratio (PEA/(±)AMNP) equal to 0.45 (Example 3) the resolution capability remains high but the yield of (+) AMNP is drastically reduced; whereas using a ratio equal to 0.75 (Example 4) and 1 (Example 5) the resolution capability tends to zero.

Example 6 shows that when the ratio is 1 increasing of the resolution capability causes a reduction of the productivity.

Finally, Example 7 shows a process which corresponds to that indicated as the preferred one by the Japanese non-examined application No. 50/55,135, excepting that the PEA/(±) AMNP ratio is 0.6 instead of 1. The yield and the optical purity are definitely lower than those obtained with a ratio equal to 1, therefore this behaviour is sharply different from that observed when chloroform is used.

EXAMPLE 1

To a mixture of 460 g (2 moles) of (±) AMNP in 1.4 l of chloroform at 40° C., 152.8 ml (1.2 moles) of PEA were added in 30 minutes. The mixture was refluxed for 30 minutes, then cooled slowly to 0° C., filtered and washed with 400 ml of chloroform. The humid salt (which gives and acid having $[\alpha]_D^{25}+54.4$ (c=1%; chloroform)) was treated at 40° C. with 900 ml of chloroform and then cooled to room temperature. After filtration, the salt was suspended in 400 ml of chloroform and 1.3 l of water and treated with 60 ml of a solution of 30% sodium hydroxide up to pH 13-14. The chloroform layer containing PEA was separated and combined with the chloroform extracts obtained from the aqueous phase. The latter was made acid up to pH 5-6 and, after filtration, 180 g (yield, 78%) of (+) AMNP having $[\alpha]_D^{25}+64.1$ (c=1%, chloroform) were obtained. The racemization of the antipode was made according to well known techniques, by heating the aqueous/alkaline solution from which the remaining PEA has been extracted with chloroform; 270 g $[\alpha]_D^{25}-1.8$ (c=1%; chloroform) (±) AMNP have been thus recovered. PEA has been recovered in chloroform solution with a yield of 90%.

EXAMPLE 2

To a mixture of 115 g (0.5 mole) of (±) AMNP in 340 ml of chloroform, cooled to 0° C., 38.2 ml (0.3 mole) of PEA were added in 45 minutes maintaining the temperature of the reaction mixture at 0° C. After 30 minutes, the mixture was filtered and washed with 100 ml of chloroform. The humid salt (which gives an acid having $[\alpha]_D^{25}+45.5$ (c=1%; chloroform)) was treated with 350 ml of chloroform at the refluxing temperature of the mixture. After cooling to room temperature, the salt was filtered and yielded, after hydrolysis and usual treatment, 40.3 g (yield, 70%) of (+) AMNP $[\alpha]_D^{25}+65.7$ (c=1%; chloroform).

EXAMPLE 3

Following the procedure of Example 1, but using 114.6 ml (0.9 mole) of PEA, 92.3 g (yield, 40%) of (+) AMNP having $[\alpha]_D^{25}+65.1$ (c=1%; chloroform) were obtained.

EXAMPLE 4

To a mixture of 115 g (0.5 mole) of (±) AMNP in 340 ml of chloroform at 40° C., 47.8 ml (0.375 mole) of PEA were added in 30 minutes. The mixture was refluxed for 30 minutes and then cooled slowly to 0° C., filtered and washed with 100 ml of chloroform. The thus obtained salt was hydrolyzed and afforded 74.7 g of (+) AMNP having $[\alpha]_D^{25}+26.5$ (c=1%; chloroform).

EXAMPLE 5

Following the procedure of Example 4, but using 63.8 ml (0.5 mole) of PEA, 108 g of (±) AMNP (rotatory power practically equal to zero) were obtained after hydrolysis.

EXAMPLE 6

To a mixture of 100 g (0.438 mole) of (±) AMNP in 850 ml of chloroform at 40° C., 57 ml (0.448 mole) of PEA were added in 30 minutes. Afterwards, following the procedure of Example 1, 37.1 g (yield, 74%) of (+) AMNP having $[\alpha]_D^{25}+65.5$ (c=1%; chloroform) were obtained.

EXAMPLE 7

To a mixture of 57.5 g (0.25 mole) of (±) AMNP in 250 ml of methanol, 19.1 ml (0.15 mole) of PEA dissolved into 800 ml of ethyl acetate were added in 15 minutes at 25° C. The mixture was left overnight at 20°-25° C., the salt was filtered and washed with 100 ml of a (2/1 w/w) mixture of ethyl acetate/methanol. 16.5 g of salt (which gives an acid having $[\alpha]_D^{25}+58.1$ (c=1%; chloroform) were obtained, which recrystallized from a mixture (6/1) of ethyl acetate/methanol afforded, after hydrolysis, 9.5 g (yield, 33%) of (+) AMNP having $[\alpha]_D^{25}+62.5$ (C=1%; chloroform).

We claim:

1. A process for the optical resolution of (±) 2-(6'-methoxy-2'-naphthyl)-propionic acid which comprises:
   (a) adding from 0.45 to 0.65 mole of (S)-alphaphenylethylamine to each mole of the acid in 3 parts ±15%, with regard to the acid, of chloroform at from 0° to 58° C.,
   (b) cooling of the reaction mixture to 0° C.,
   (c) filtering the thus obtained precipitate,
   (d) suspending the filtrate in chloroform at 15°–58° C.,
   (e) cooling of the reaction mixture,
   (f) filtering the thus obtained precipitate,
   (g) again suspending the precipitate in chloroform and treating this suspension with an aqueous alkaline solution,
   (h) separating the chloroform phase from the aqueous phase, and
   (i) treating the aqueous phase with acid to yield (+) 2-(6'-methoxy-2'-naphthyl)-propionic acid and recovering same.

2. The process according to claim 1 including the additional steps of:
   (j) treating the chloroform solution of preceding step (c) with an aqueous/alkaline solution,
   (k) separating the chloroform phase from the aqueous phase, and
   (l) heating the aqueous phase of step (k) to yield (±) 2-(6'-methoxy-2'-naphthyl)-propionic acid which is recycled.

3. The process according to claim 2 including the additional step of:
   (m) recycling the chloroform solution of preceding step (f), without treatment, to carry out step (a).

4. The process according to claim 2 including the further step of:
   (n) recycling the chloroform solution of (S)-alpha-phenylethylamine obtained in preceding steps (h) and (k) optionally after evaporation to the desired concentration.

* * * * *